US00PP33781P2

(12) United States Plant Patent
Hansen

(10) Patent No.: US PP33,781 P2
(45) Date of Patent: Dec. 21, 2021

(54) ***SEDUM* PLANT NAMED 'TIRAMISU'**

(50) Latin Name: ***Sedum* hybrid**
Varietal Denomination: Tiramisu

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,509

(22) Filed: Jul. 27, 2021

(51) Int. Cl.
*A01H 5/12* (2018.01)
*A01H 6/32* (2018.01)

(52) U.S. Cl.
USPC ..... Plt./479

(58) Field of Classification Search
USPC ..... Plt./479
See application file for complete search history.

*Primary Examiner* — Susan McCormick Ewoldt

(57) ABSTRACT

A new and distinct ornamental perennial *Sedum* plant named 'Tiramisu' is characterized by tight-forming upright mounds of mostly vertical stems with dark-green to greyed-purple glaucous foliage that resists powdery mildew and subsequent scaring. The numerous, dark, greyed-purple stems produce tall inflorescences that resist lodging in summer heat and rains. Individual cream-colored flowers emerge from light-pink blushed buds. The new plant is useful for the landscape in containers, as specimens or en masse.

1 Drawing Sheet

Botanical designation: *Sedum* hybrid.
Cultivar denomination: 'Tiramisu'.

STATEMENT REGARDING PRIOR DISCLOSURES UNDER 37 CFR 1.77(B)(6)

The claimed plant was first sold to Willoway Nurseries, Inc. on Jul. 31, 2020 by Walters Gardens, Inc., who obtained the plant and all information relating thereto, from the inventor. Subsequently the new plant was also sold to Prides Corner Farms and Overdevest Nurseries, LP. The first non-enabling description and photographs were on a website operated by Walters Gardens, Inc. on Dec. 1, 2020, and on May 20, 2021 in the "Walters Gardens 2021-2022 Catalog." No plants of *Sedum* 'Tiramisu' have been sold in this country or anywhere in the world, nor has any disclosure of the new plant been made, more than one year prior to the filing date of this application, and such sale or disclosure within one year was either derived directly or indirectly from the inventor and would be a 35 U.S.C. § 102(b) exception.

BACKGROUND OF THE INVENTION

The present invention relates to a new and distinct cultivar of *Sedum* plant, botanically known as *Sedum* and hereinafter referred to by the cultivar name 'Tiramisu'.

The new *Sedum* plant is a selection of a planned breeding program conducted by the inventor, at a wholesale perennial nursery in Zeeland, Mich., USA.

The new *Sedum* plant was selected from a controlled insect pollination cross in an isolation block of a proprietary, unreleased, unnamed hybrid known only by the breeder code 13-91-1 with an unidentified sibling of 13-91-1 at a wholesale perennial nursery in Zeeland, Mich. The seeds were collected on Oct. 8, 2014. *Sedum* 'Tiramisu' was assigned the breeder code number 14-86-5 to keep it separated from among thousands of other seedlings of this and other crosses when it progressed through the initial trial phase in the fall of 2016. The selected single seedling clone was originally selected for it strong, healthy, dense growth, colorful foliage and flowers and intermediate traits between the two parents.

Asexual reproduction of *Sedum* 'Tiramisu' by division at a wholesale perennial nursery in Zeeland, Mich., USA since October of 2016, and subsequent vegetative shoot tip cuttings has shown that the unique features of this new *Sedum* plant are stable and reproduced true to type in successive generations.

SUMMARY OF THE INVENTION

Plants of *Sedum* 'Tiramisu' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of *Sedum* 'Tiramisu' and distinguish it as a new and distinct Autumn Stonecrop plant unique from all other Autumn Stonecrop plants known to the inventor:

1. Tight-forming upright mounds with mostly vertical stems;
2. Center stems remain erect throughout the growing season producing full habit;
3. Glaucous, dark-green to grey-purple foliage resists powdery mildew and the subsequent scaring;
4. Numerous, stems produce tall inflorescences with small flower clusters of creamy-colored flowers from light pink blushed flower buds.
5. Flower buds are light green opening to pale cream with rosy pink center ovaries;

The nearest comparison varieties known to the inventor are: 'Back in Black' copending U.S. Plant patent application Ser. No. 17/300,220, 'Xenox' U.S. Plant Pat. No. 16,888, 'Black Jack' U.S. Plant Pat. No. 16,736, 'Night Embers'

U.S. Plant Pat. No. 29,211, 'Touchdown Teak' U.S. Plant Pat. No. 26,078, 'Dark Magic' U.S. Plant Pat. No. 27,619, 'Spellbound' copending U.S. Plant patent application Ser. No. 17/300,288 and 'Coraljade' copending U.S. Plant patent application Ser. No. 17/300,513.

'Back in Black' has flowers of light-pink with deep garnet carpels and has a more greyed-purple foliage coloration. 'Xenox' has less branching and is prone to lodging. 'Black Jack' has dark mahogany foliage, shorter inflorescences of more reddish flowers and the foliage is more prone to powdery mildew. 'Night Embers' has foliage that is less glaucous, more glossy and dark black-purple with a less-branching narrower habit. 'Touchdown Teak', 'Dark Magic' is smaller in habit with smaller leaves that are less glaucous greyed-purple with thinner stems. 'Spellbound' has a shorter more compact habit with foliage that is more greyed-green. 'Coraljade' has a more rounded habit with flower buds that begin citron-green and mature to a coral-pink.

In comparison, the female parent was not as full and did not retain the upright stems as well as the new plant through the entire growing season. The male parent was unknown but may have been any one of a number of other cultivars or proprietary hybrids in the breeding area, but also and a tendency to lodge later in the season.

BRIEF DESCRIPTION OF THE PHOTOGRAPHS

The photograph of the new plant demonstrates the unique traits and the overall appearance of *Sedum* 'Tiramisu'. The colors are as accurate as reasonably possible with color reproductions of this type. Variations in ambient light spectrum, source and direction may cause the appearance of minor variation in color. The plants used in the photograph were three-year-old plants grown in an open, full-sun trial garden at a wholesale perennial nursery in Zeeland, Mich. with supplemental water and fertilizer when needed. No plant growth regulators or pinching have been used.

DETAILED BOTANICAL DESCRIPTION

Figure 1:
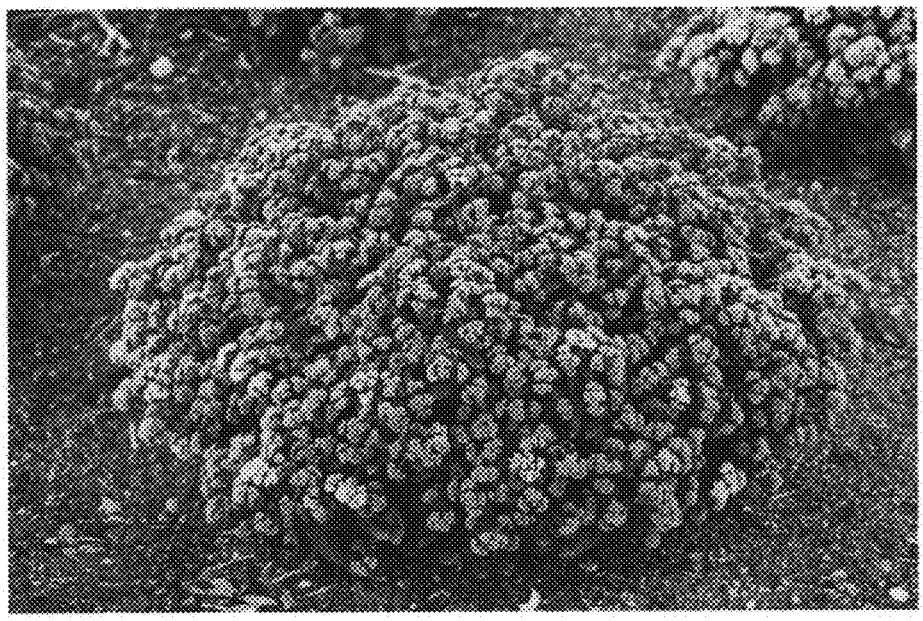
FIG. 1 shows the habit of the new plant with foliage in early stages of flowering.
Figure 2:
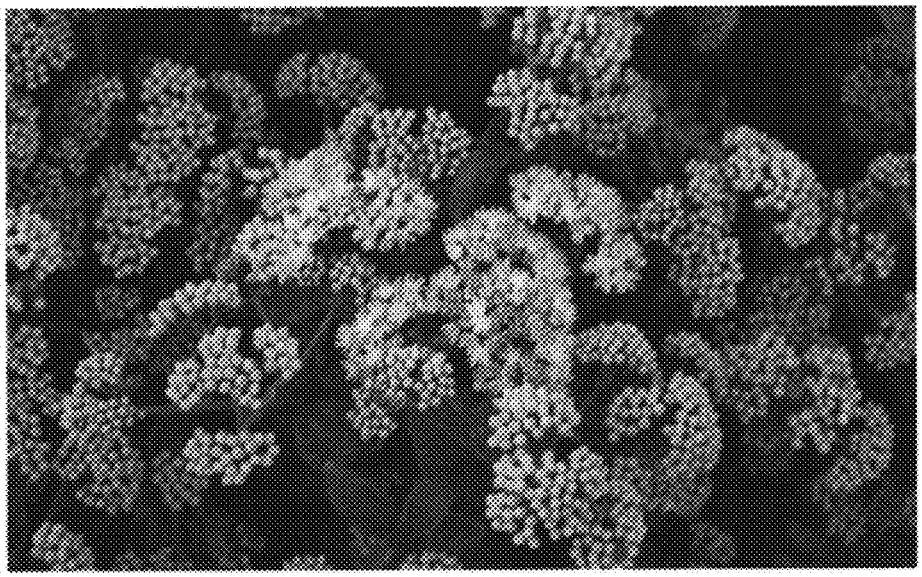
FIG. 2 shows a close-up of the flowers and buds of the new plant in late-summer.

The following is a detailed description of three-year-old plants of the new cultivar as grown outdoors in a full sun trial plot at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Parentage: A selection of the unreleased, unnamed proprietary hybrid known only by the breeder code 13-91-1 as the female parent and the male parent was an unidentified sibling of 13-91-1 from the controlled breeding area;

Asexual propagation: Stem tip cuttings and division;

Time to initiate roots: About two weeks;

Time to finish a 3.8 liter flowering container: About three months in the summer from a rooted 2.5 cm plug;

Root description: Thick, fleshy; freely branching; creamy white to light tan in color;

Plant habit: Winter-hardy herbaceous perennial; upright mound; stiff upright stems; dense and full, not opening in center later in the season; flower heads freely branching;

Growth rate: Moderately vigorous;

Plant size: About 65.0 cm tall and 72.0 cm wide in full flower;

Stems: Terete; glaucous; glabrous; diameter at base to about 13.0 mm, average about 11.0 mm; heavily branched in distal portion; about 15.0 cm long from base to initial branches; about 12 stems per plant and 22 branches per stem;

Stem color: Proximally or in shade between RHS 145A and RHS 146D, distally between RHS 187C to RHS N187A;

Lateral branches: To about 22 per stem; glaucous; glabrous; terete; primary branches to about 20.0 cm long and about 6.0 mm diameter at base;

Lateral branch color: Proximally or in shade between RHS 145A and RHS 146D, distally variable between RHS N187A and RHS 187C;

Foliage: Ovate to elliptic; spirally arranged; simple; smooth; sarcous; slightly twisted along longitudinal axis; glabrous and glaucous on both surfaces; sessile; thick; apex bluntly acute to rounded; base attenuate; margin irregularly and shallowly dentate, 6 to 8 teeth per leaf side; teeth about 8.0 mm to 10.0 mm apart; decreasing in size distally; attitude outward; about 14 leaves per stem before inflorescence branches;

Foliage size: To about 7.2 cm long, 3.3 cm across and 2.5 mm thick; average about 6.2 cm long, 4.9 cm across and 3.0 mm thick; decreasing distally;

Foliage color: Adaxial young nearest RHS 138B, abaxial young between RHS N138D and RHS 138B, with a thin margin or side of leaf nearest RHS 187B; mature adaxial nearest RHS NN137C with strong blush to nearly solid overtone of nearest RHS 187B, mature abaxial between RHS 147B and RHS 147C variably maculate or blushed with nearest RHS 187B; and margin or leaf side blushed to solid RHS 187B Petiole: Leaves sessile;

Venation: Palmate, barely distinguishable; slightly raised abaxial;

Vein color: Adaxial midrib nearest RHS 187B and abaxial midrib nearest RHS 146D variably blushed with nearest RHS 187B; secondary veins not obvious;

Flower: Stellate, actinomophic; pentamerous; persistent; attitude upright to outwardly in terminal compound cymes; size about 8.0 mm across and 7.0 mm deep;

Flower number: About 60 to 75 per branch and 800 to 1,200 flowers per stem and 6,000 to 12,000 per plant;

Fragrance: None detected;

Flowering season: Beginning late-summer in Zeeland, Michigan for about three weeks;

Longevity: Flower cymes remain effective for about three weeks on the plant and one week as cut flowers; individual flowers and calyces persistent and effective for about three weeks;

Flower buds about one day prior to opening: Ellipsoidal; apex acute; base truncate; about 5.0 mm long and about 3.0 mm diameter near middle;

Flower bud color: Between RHS 65A and RHS 65B; calyx between RHS 189A and RHS N187C;

Inflorescence: To about 30.0 cm tall from first branch and about 20.0 cm across; up to about 1,200 flowers per inflorescence;

Petals: Typically five; broadly-lanceolate; acute apex; base truncate and fused; margin entire; glabrous abaxial and adaxial; to about 5.5 mm long and about 2.5 mm across at fusion;

Petal color: Young adaxial and abaxial nearest RHS N155B; adaxial maturing to nearest RHS NN155C along margins and nearest RHS N155B along the longitudinal center; abaxial maturing to between RHS NN155C and RHS 65D in longitudinal center and between RHS 65D and RHS NN155D along margins;

Calyx: With five sepals; campanulate to stellate; about 4.5 mm across and 3.5 mm deep;

Sepals: Linear to lanceolate; narrowly acute apex; fused base; entire margin; glabrous and slightly glaucous both abaxial and adaxial; adpressed to petals, about 3.0 mm long and about 1.0 mm across;

Sepal color: Abaxial and adaxial nearest RHS 191A blushed with N187C;

Peduncles: Terete; glaucous; glabrous; stiff and flexible; freely branching; mostly; with branches to about 45° to 60° above horizontal; about 30.0 cm long and 6.0 mm diameter below first branches;

Peduncle color: Between RHS 187B and RHS N187A;

Pedicels: Cylindrical; glabrous; glaucous; strong and stiff, yet flexible; average about 5.0 mm long and 0.7 mm diameter;

Pedicel color: Blend between RHS N187B and RHS N138D;

Androecium: Typically ten stamens;

*Filaments*.—Cylindrical; outwardly; alternately free to fused to inner corolla in basal 1.0 mm; about 4.5 mm long and about 0.3 mm diameter; color between RHS N155B and RHS NN155B.

*Anthers*.—Basifixed; longitudinal; ellipsoidal; about 0.7 mm long and 0.5 mm diameter; color nearest RHS 8D.

*Pollen*.—Moderate in quantity; color nearest RHS 8C.

Gynoecium: Typically five; cylindrical, conic in distal one third; about 5.5 mm long and 1.2 mm diameter;

*Style*.—Terete; ellipsoidal, tapering distally and base truncate; about 2.0 mm long and 0.5 mm diameter at point of attachment to ovary; glabrous; lustrous; color beginning nearest RHS N155B and maturing to nearest RHS 65D.

*Stigma*.—Minute, acute; about 0.2 mm diameter and 0.2 mm long; color nearest RHS 65D.

*Ovary*.—Nearly terete, acutely tapering at apex to style; base truncate; lustrous; about 3.0 mm long and 1.2 mm diameter; color beginning nearest RHS 2D and maturing to nearest RHS 63B.

Fruit: Ventrally dehiscent follicle; about 3.5 mm long and 3.2 mm across; color at maturity nearest RHS 177A;

Seed: Sparse; fine; lanceolate; about 1.0 mm long and less than 0.2 mm across; color between RHS 165A and RHS 165B;

Growing conditions: Plants of 'Tiramisu' are xeromorphic and grow best with good drainage, full sun and moderate to low fertility. The new plant is cold hardy from USDA zones 3 to 9 and has tolerated temperatures of at least 35 degrees C. 'Tiramisu' tolerates heavy rains and wind and is not prone to develop an open center later in the season as many other *Sedum* cultivars do that are known to the inventor.

Disease and pest resistance: Other pest and disease resistance and tolerance outside that normal for *Sedum* is not known.

It is claimed:

1. A new and distinct perennial *Sedum* plant named 'Tiramisu' as herein described and illustrated.

* * * * *